United States Patent [19]
Ku

[11] Patent Number: 5,211,665
[45] Date of Patent: May 18, 1993

[54] ACETABULAR CUP ASSEMBLY FOR TOTAL HIP REPLACEMENT

[76] Inventor: Ming C. Ku, P.O. Box 82-144, Taipei, Taiwan

[21] Appl. No.: 845,397

[22] Filed: Mar. 4, 1992

[51] Int. Cl.$^5$ ............................................. A61F 2/34
[52] U.S. Cl. ................................................. 623/22
[58] Field of Search .................... 623/22, 23, 18, 16

[56] References Cited
U.S. PATENT DOCUMENTS

| | | | |
|---|---|---|---|
| 4,828,565 | 5/1989 | Duthoit et al. | 623/22 |
| 4,840,632 | 6/1989 | Kampner | 623/22 |
| 4,871,368 | 10/1989 | Wagner | 623/18 X |
| 5,021,062 | 6/1991 | Adrey et al. | 623/16 X |

Primary Examiner—David Isabella
Attorney, Agent, or Firm—Alfred Lei

[57] ABSTRACT

This invention relates to an acetabular cup assembly for total hip replacement and in particular to one including a generally hemispherical socket provided with a tubular neck having internal threads at the lower portion and a plurality of webs around the tubular neck, and a stud adapted to be inserted through the tubular neck of the hemispherical shell member and provided on the upper portion with external threads engageable with the internal threads of the tubular neck, whereby the acetabular cup assembly may be firmly fixed on the bone.

5 Claims, 4 Drawing Sheets

ACETABULAR CUP ASSEMBLY FOR TOTAL HIP REPLACEMENT

BACKGROUND OF THE INVENTION

It is found that loosening of the acetabular cup in cemented total hip replacement often happens about 5-10 years after operation. As more and more prostheses have been mounted into yound and bone deficient hips nowadays, revision cases for replacing the loosened acetabular cup have become significant part of daily work of hip surgeons. Bone loss caused by loosened cup in cemented hip as well as uncemented hip, together with bone defect in dysplastic and protrusio hip are now the main concerns of surgeons.

In comparision with the femoral stem, much less attention has been paid to the fixation of acetabulum. Although the benign behavior of a radiologically loosened acetabular cup has given clinicians false impression in short term, the difficulties in reconstruction of bone deficiency and the poor results after massive bone graft at long run in loosened cup have alarmed surgeons to face the problems earlier on. At present the only way to manage massive bone loss is bone graft either by segmental bone or bone chips, maybe an autograft or allograft. Then, how to protect the bone graft may be the only way to get out of the mess.

Stemmed tibial tray in TKR has been proved of the capability to enhance the fixation of the tray from lossening either biomechanically or clinically. Based on the same principle and studies of the comparative anatomy of the pelvic bone, it is believed that the iliopubic bone bar similar to the diaphysis of long bones is the best part for the fixation of a stemmed prosthesis for the pelvis.

Therefore, it is an object of the present invention to provide an improved acetabular cup assembly which may obviate and mitigate the above-mentioned drawbacks.

SUMMARY OF THE INVENTION

This invention relates to an improved acetabular cup assembly for total hip replacement.

It is the primary object of the present invention to provide an acetabular cup assembly which has a detachable stud.

It is another object of the present invention to provide an acetabular cup assembly which can be firmly fixed on the bone.

It is still another object of the present invention to provide an acetabular cup assembly which will offer the best protection for the bone graft as well as weakened bone.

It is still another object of the present invention to provide an acetabular cup assembly which is simple in construction.

It is a further object of the present invention to provide an acetabular cup assembly which is economic to produce.

Other objects and merits and a fuller understanding of the present invention will be obtained by those having ordinary skill in the art when the following detailed description of the preferred embodiment is read in conjunction with the accompanying drawings.

DETAILED DESCRIPTION OF THE PREFERRED EMBODIMENT

Before explaining the present invention in detail, it is understood that the invention is not limited in its application to the details of construction and arrangement of parts illustrated in the accompanying drawings, since the invention is capable of other embodiments and of being practiced or carried out in various ways. Also it is to be understood that the phraseology or terminology employed herein is for the purpose of description and not of limitation.

Figure 1:
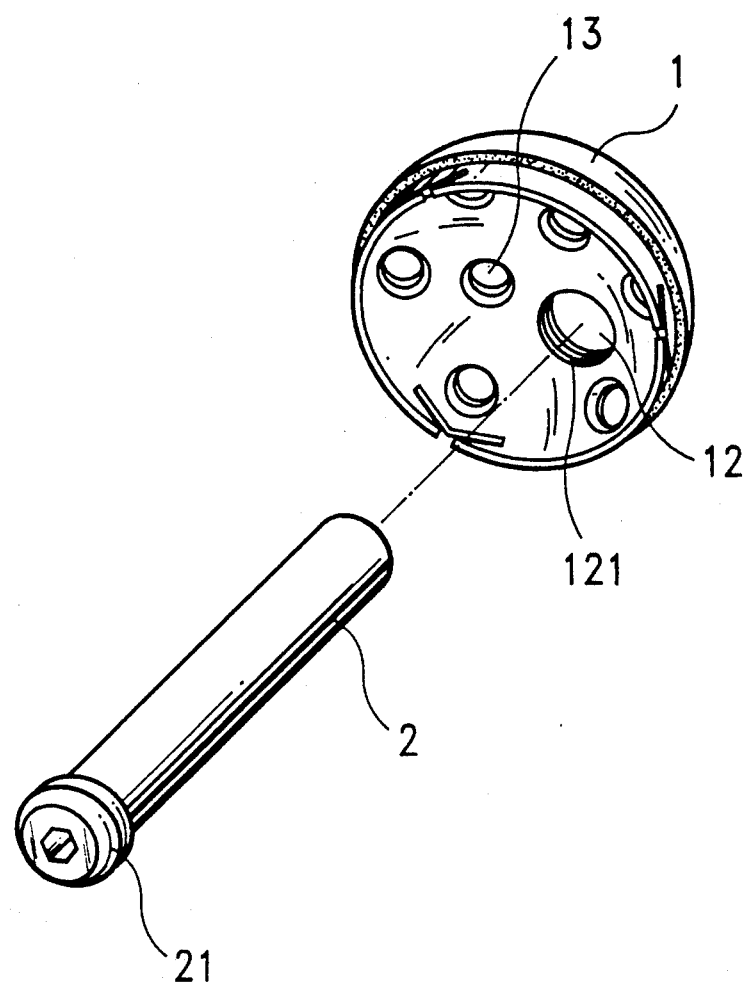
FIG. 1 is a exploded view of an acetabular cup assembly according to the present invention.
Figure 2:
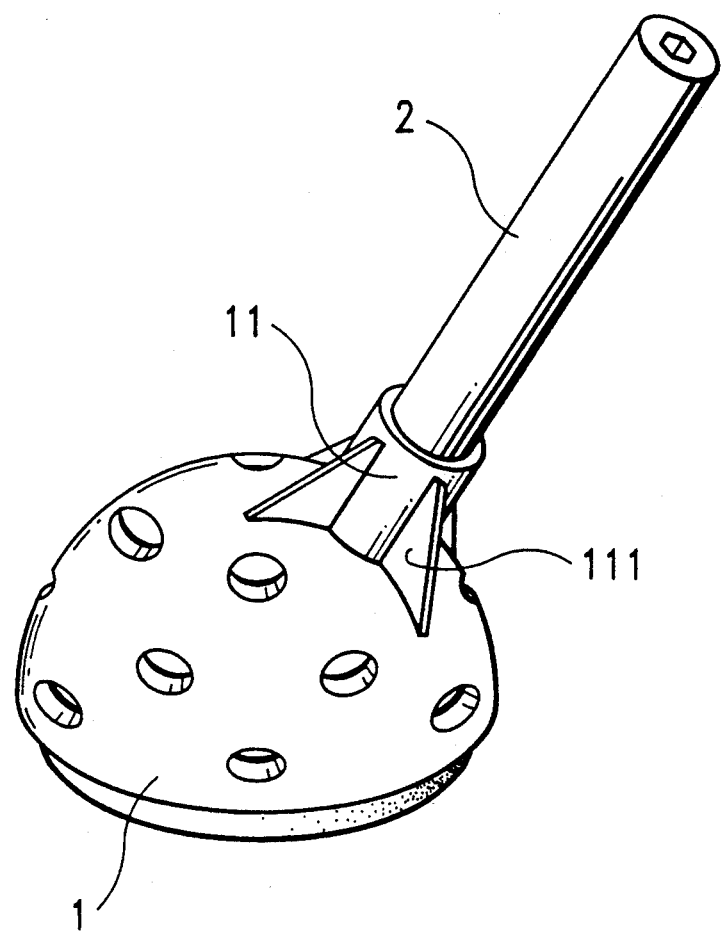
FIG. 2 is a perspective view of the present invention.
Figure 3:
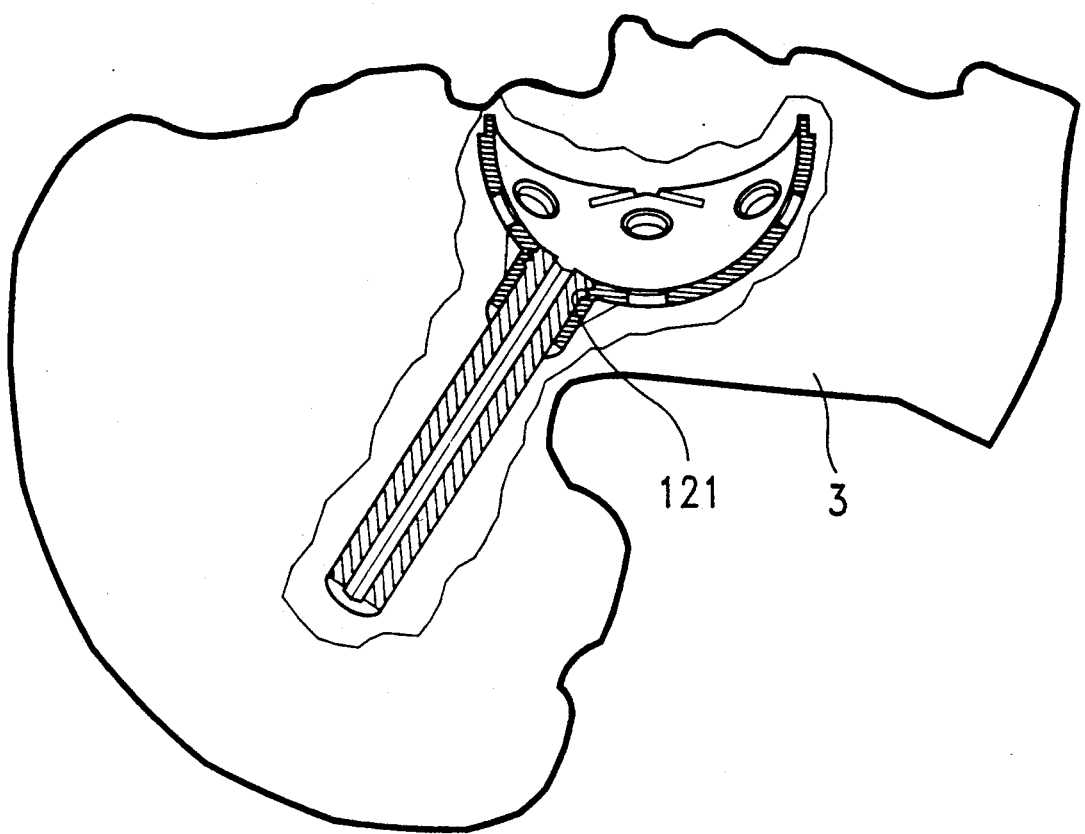
FIG. 3 is a working view of the present invention.
Figure 4:
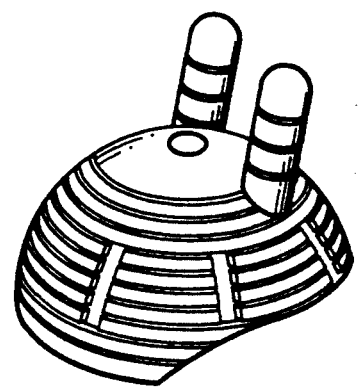
FIGS. 4-6 show prior art acetabular cup assemblies.
Figure 5:
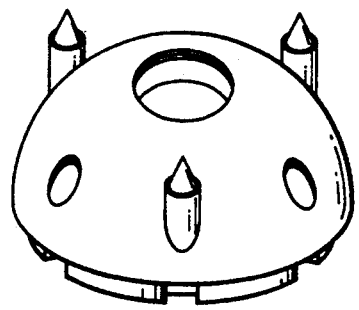
Figure 6:
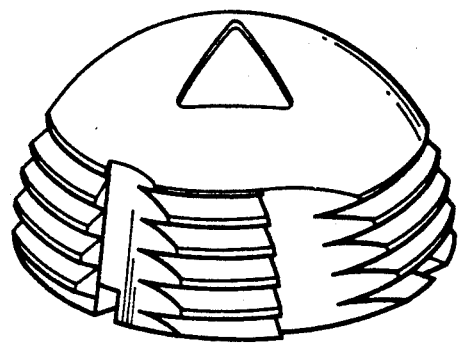

With reference to the drawings and in particular to FIGS. 1 and 2, the acetabular cup assembly according to the present invention mainly comprises a socket 1 and a stud 2. The socket 1 is a generally hemispherical shell member on the upper surface of which there is a tubular neck 11 and a plurality of perforations 13. Around the tubular neck 11 there are a plurality of webs 111. The tubular neck 11 and the webs 111 are welded or otherwise secured on the socket 1. Preferably, the tubular neck 11 is integrally formed with the socket 1. A hole 12 extends through the tubular neck 11 and the socket 1 and is provided with internal threads 121 at the lower portion thereof.

In this embodiment, the tubular neck 11 is located so that its center line makes an angle of 45 degrees with the center line of the socket 1.

The stud 2 is adapted to be fitted with the hole 12 and is provided at the upper portion with external threads 21 so that the stud 2 may be inserted through the tubular neck 11 and kept in rigidly fixed connection with the socket 1. Further, the upper end of the stud 2 may be provided with a hexagonal recess so as to make it easier to turn the stud 2 to engage with the socket 1.

Although the present invention has been described with a certain degree of particularity, it is understood that the present disclosure is made by way of example only and that numerous changes in the detail of construction and the combination and arrangement of parts may be resorted to without departing from the spirit and scope of the invention as hereinafter claimed.

I claim:

1. An acetabular cup assembly for total hip replacement comprising:
    a generally hemispherical shell socket provided with a tubular neck thereon, said tubular neck having internal threads at a lower portion, a plurality of webs around the tubular neck and a hole extending through the tubular neck and the hemispherical shell socket; and
    a stud adapted to be inserted through the tubular neck of said hemispherical shell socket and provided on an upper end with external threads engageable with the internal threads of said tubular neck.

2. The acetabular cup assembly for total hip replacement as claimed in claim 1, wherein said hemispherical shell socket is provided with a plurality of perforations thereon.

3. The acetabular cup assembly for total hip replacement as claimed in claim 1, wherein said stud has a hexagonal recess on said upper end thereof.

4. The acetabular cup assembly for total hip replacement as claimed in claim 1, wherein said tubular neck is formed integrally with the hemispherical shell socket.

5. The acetabular cup assembly for total hip replacement as claimed in claim 1, wherein said tubular neck has a center line which makes an angle of 45 degrees with a center line of said hemispherical shell socket.

* * * * *